United States Patent [19]

Modrovich

[11] 4,378,429

[45] Mar. 29, 1983

[54] ENZYMATIC METHOD AND STABILIZED SOLUTIONS FOR DETERMINING TOTAL CHOLESTEROL IN HUMAN SERUM

[76] Inventor: Ivan E. Modrovich, 1043 Mesa Dr., Camarillo, Calif. 93010

[21] Appl. No.: 294,987

[22] Filed: Aug. 21, 1981

Related U.S. Application Data

[63] Continuation-in-part of Ser. No. 68,911, Aug. 23, 1979, abandoned.

[51] Int. Cl.³ ............... C12Q 1/60; C12Q 1/44; C12Q 1/28; C12N 9/96
[52] U.S. Cl. .......................... 435/11; 435/19; 435/25; 435/28; 435/188; 435/810; 252/408.1
[58] Field of Search ............... 435/11, 19, 188, 25, 435/28, 810; 23/230 B; 252/408 R

[56] References Cited

U.S. PATENT DOCUMENTS

| | | | |
|---|---|---|---|
| 3,876,375 | 4/1975 | Maurukas | 252/408 |
| 3,907,642 | 9/1975 | Richmond | 435/11 |
| 3,907,645 | 9/1975 | Richmond | 435/11 |
| 3,925,164 | 12/1975 | Beaucamp et al. | 435/11 |
| 4,102,742 | 7/1978 | Klose et al. | 435/11 |
| 4,121,905 | 10/1978 | Maurukas | 252/408 |
| 4,153,511 | 5/1979 | Modrovich | 435/188 |
| 4,161,425 | 7/1979 | Perry | 435/11 |
| 4,164,448 | 8/1979 | Röeschlau | 435/11 |
| 4,226,713 | 10/1980 | Goldberb | 435/11 |
| 4,325,832 | 4/1982 | Louderback | 252/408 |

FOREIGN PATENT DOCUMENTS 52-14490  2/1977  Japan ..................... 435/11

OTHER PUBLICATIONS

Allain, C. C. et al., "Enzymatic Determination of Total Serum Cholesterol", Clinical Chem., vol. 20, No. 4, pp. 470–475, (1974).

*Primary Examiner*—Benoit Castel
*Attorney, Agent, or Firm*—Christie, Parker & Hale

[57] ABSTRACT

Stabilized enzymes useful in the diagnostic assay of total cholesterol are prepared by dissolving a salt of cholic acid in a buffer solution providing a pH within the range of about 4 to about 9, to the solution is added a cholesterol esterase. The solution is then mixed with a polyhydroxy organic compound and TRITON-X-100. A cholesterol oxidase and a peroxidase are each dissolved in separate portions of buffer solution and introduced into the buffered solution containing the cholesterol esterase. 4-aminoantipyrine is then added to the solution. The resultant solution is a stabilized enzyme solution which can be used in the total cholesterol assay of a serum sample. The stabilized solution can be used in combination with a chromogen diluent solution which is made by dissolving phenol and TRITON-X-100 in water or a buffer solution. The combination of the stabilized enzyme solution and the chromogen diluent solution provides a solution which has utility in the spectrophotometric assay of total cholesterol.

80 Claims, No Drawings

ENZYMATIC METHOD AND STABILIZED SOLUTIONS FOR DETERMINING TOTAL CHOLESTEROL IN HUMAN SERUM

CROSS REFERENCE TO RELATED APPLICATIONS

This application is a continuation-in-part of application Ser. No. 06/068,911 filed Aug. 23, 1979, and is related to application Ser. No. 06/168,204 filed July 10, 1980, both incorporated herein by reference, and both abandoned.

BACKGROUND OF THE INVENTION

The present invention relates to a method for determining cholesterol, either total cholesterol or bound cholesterol, in human serum. More particularly, the invention relates to a method and stabilized enzymatic solutions for use in the method in determining the total cholesterol in serum.

Cholesterol is present in biological matter, such as serum and the like, partially in free form and partially in bound form as a cholesterol ester. For the determination of total cholesterol, it is necessary to release the cholesterol that is bound in cholesterol ester form. The releasing of the bound cholesterol has been conducted through saponification of the cholesterol ester under alkaline conditions using alcoholic potash lye, for example. Following the saponification, the released cholesterol can then be determined either chemically or enzymatically by one of the known methods. A chemical determination may be performed, for example, by the Liebermann-Burchard method. An enzymatic determination may be performed by means using cholesterol oxidase, cholesterol esterase, or cholesterol dehydrase.

The alkaline saponification of bound cholesterol is a troublesome and time consuming step in the overall assay of total cholesterol. Furthermore, the relatively agressive reagents used may lead to a decomposition of the cholesterol. In order to prevent such decomposition and inhibit the determining of false and/or imprecise results of the analysis, a hydrolysis must generally be performed under relatively mild conditions. This, in turn, undesirably increases the length of time required for the cholesterol determination. The alkaline liberation of the bound cholesterol is especially disadvantageous when the determination of the cholesterol is to be performed by the preferred enzymatic methods. Since the enzymes are inactivated in the strongly alkaline medium, the hydrolyzate must be neutralized by the addition of acid to a pH of about 5 to 8 before the enzymatic determination can be initiated. This extra step results in the addition of more time in the overall determination of the total cholesterol.

It is also known that bound cholesterol can be freed by the action of enzymes, cholesterol esterases, which break the ester bond in cholesterol esters. Such cholesterol esterases were isolated initially from animal sources, such as from pork pancreas and rat pancreatic juice. It is also known that in addition to cholesterol esterases being found in the pancreas, that cholesterol esterases can be found in the liver.

Allain, et al. describe an enzymatic method for the determination of total serum cholesterol using a cholesterol esterase isolated from pork pancreas and rat pancreatic juice. "Clinical Chemistry," 20 (1974), 470–475. In the method of Allain, et al. the cholesterol esterase (cholesterol ester hydrolyase), freed the esterified cholesterol. The resulting freed cholesterol was treated with cholesterol oxidase to form cholestenone and hydrogen peroxide. The resulting hydrogen peroxide was measured quantitatively using spectrophotometric methods. The hydrogen peroxide reacted with 4-aminoantipyrine and phenol in the presence of a peroxidase to form a quinoneimine dye. Allain, et al. utilized one aqueous buffered solution to conduct the cholesterol determinations. Cholesterol esterases are known labile compounds that are generally unstable in aqueous solutions. Allain, et al. state that the enzyme solution used in their method is unstable having a stability of eight hours at room temperature (25° C.) and 24 hours at refrigerated temperatures of 4° C.

U.S. Pat. No. 3,925,164 to Beaucamp, et al. also describes a method for the enzymatic determination of total cholesterol in serum. The method therein treats the serum sample with a cholesterol esterase to release the bound cholesterol. The total cholesterol is then determined by known techniques. The method utilizes a cholesterol esterase produced from a microorganism rather than using a cholesterol esterase produced from an animal source. The patent states that the microorganism produced cholesterol esterase is preferred over cholesterol esterase produced from animal sources in the complete saponification of cholesterol esters in the framework of a quantitative analysis process because the cleavage rates for animal source cholesterol esterases were not quantitative. Furthermore, bound cholesterol is present in biological matter in the form of widely different acids. For an enzymatic process to be useful in the framework of a process of quantitative analysis, it is required that all of the esters that may occur be cleaved quantitatively with approximately the same speed and with the same reliability. Many of the known animal-source cholesterol esterases are somewhat specific toward specific cholesterol esters. The activity of such cholesterol esterases is known to vary with regard to various cholesterol esters.

Although the cholesterol esterases produced from microorganisms offer advantages over those produced from animal sources, the microorganism-produced cholesterol esterases also are labile compounds that tend to undergo chemical change in solution and especially in aqueous solutions, which decreases their enzymatic activity. Stability of enzymatic solutions used in diagnostic assays is important in providing methods of analysis which exhibit precision and uniformity among separate determinations when conducted over a period of elapsed time. Instablity of enzymatic solutions, in addition to not providing reproducibility of assays, can also add to the ever increasing cost of medical services because the unstable enzymatic solutions need to be discarded and fresh solutions formulated.

It has recently been estimated that about 25 percent of all in vitro diagnostic tests conducted annually in the United States are unreliable. Unreliable tests can result in unnecessary medical treatment, the withholding of necessary treatment and lost income. Because of their high specificity, the use of enzyme determinations has significantly increased during the last few years and indications are that this trend will continue. However, rigorous quality control measures are required to assure the accuracy and consistency of results. This requirement derives from the fact that the exact nature of enzymes, as well as mechanisms of their reactions, remains unknown for the most part.

At present, the greatest limitation in the diagnostic reagent manufacture, by far, lies in the unstable characteristics of the enzymatic solutions. Current cholesterol diagnostic methodologies require the use of labile ingredients whether utilizing enzymes from microorganisms or animal source. Due to the labile nature of the enzymes, rigorous quality control is required over the production of such enzymatic solutions and in the reconstituting dry media preparations and formulation of such enzymatic solutions. Such quality control is costly. Moreover, if such control in any step in the process is not maintained within a high degree of control standards, the quality of the final product can be reduced materially leading to decreased precision in assay results.

The present commercial state-of-the-art used for stabilizing the reactive ability of enzymes or coenzymes is by locking them into a solid matrix, either by freeze drying, dry blending such as used for tableting dry powders primarily in the pharmaceutical diagnostic and related industries, and immobilization by locking the chemical structure of the enzyme into a solid matrix. Contrary to the sophistication these terms imply, these approaches are neither practical nor desirable and are also expensive. The manufacturer is forced to remove the water and supply a partial product, thus relinquishing part of the quality control cycle in the dilution and use of the final product. Laboratories are forced to pay the high cost of packaging, reagent waste, freeze drying and dry blending. Usefulness of the product is further limited by packaging modes and sizes.

Furthermore, good product uniformity is difficult to achieve, especially in the laboratories where the products are to be utilized in diagnostic assay. This condition is exemplified by the fact that most commercial freeze-dried controlled sera (reference serum) lists the acceptable bottle-to-bottle variation of enzyme constituents at ±10 percent of the mean.

The present invention is uniquely designed so that the enzyme solution, although containing labile ingredients in a liquid reagent, are effectively "stabilized" thereby controlling the activity of the labile ingredients in the liquid solution. The means of stability insures long-term stability in a liquid media. Moreover, close tolerance control can be achieved in the manufacturing of a high quality product which eliminates the inconvenience of the rigid package size, the high cost of packaging and freeze drying, and reagent waste.

SUMMARY OF THE INVENTION

Labile enzymes, useful in the diagnostic assay of total cholesterol in serum, are treated according to the invention resulting in long-term stability without deleteriously affecting enzyme activity or photometric absorptivity. The invention provides reagents wherein quality control is assured throughout manufacturing, packaging, storage, and the use. The inconvenience of rigid package size is eliminated as is the high cost of packaging, freeze drying, and reagent waste. The liquid enzyme system for total cholesterol assay, as described herein, provides desired flexibility to total cholesterol assay determination. The stabilized enzymes of the invention have been assessed in studies which compared the liquid stabilized enzyme solutions with fresh reagents. The studies show a one-to-one correlation between aged liquid and fresh reagents with comparable sensitivity and precision. Providing reagents of this type in a stable liquid form enhances the color of spectrophotometric capability of present-day methodologies, as well as other non-color methodologies. The stable liquid enzymes for total cholesterol determination are especially advantageous where oxygen consumption and/or hydrogen peroxide production and consumption are the bases of measurement. The liquid system of the present invention also offers better reagent homogeneity and packaging, as well as flexibility and usage, in contrast to the freeze dried or dry media preparations.

In diagnostic cholesterol assay, the stabilization of the labile components and particularly the labile cholesterol esterases in a ready-to-use liquid media, is a new and exciting approach to satisfy the needs of the clinical laboratory and the reliability demands of the regulatory authorities. The flexibility of these liquid systems insures their applicability to automated instrumentation, as well as their convenience in manual testings.

In accordance then with the present invention, there are provided stabilized aqueous enzyme solutions for use in determining of total cholesterol. The solutions are aqueous buffered solutions of a pH from about 4 to 9 and comprise a surfactant present in an amount up to about 2.5 percent by volume of solution and an effective amounts of a salt of cholic acid, preferably sodium cholate, cholesterol oxidase, cholesterol esterase, and a polyhydroxy organic compound present in an amount insufficient to materially reduce the enzyme activity of the cholesterol esterase and cholesterol oxidase.

In the concentrated form the solution polyhydroxy organic compound may be present in an amount from about 7.5 or less to about 50 percent or more by volume of the solution. The presently preferred polyhydroxy organic compounds are glycerol, ethylene glycol, sorbitol and propylene glycol. They serve to stabilize the solution against degradation and are present in sufficiently concentration such that the solutions of the instant invention will remain stable for periods up to about two years under refrigerated conditions (about 4° C.) or up to four months at room temperature, up to one week at 37° C. and 24 hours at 41° C. Long shelf life is also not destroyed by diluting the concentration normally in a normal 4:1 ratio of distilled water to concentrate.

The basic solution as set forth above is that employed for determining of total cholesterol by oxygen measurement. Where it is desired to employ a chromogen, the chromogen ingredients can be in separate solutions or combined in the basic solution. 4-aminoantipyrine combined with oxidase as the enzyme and phenol act to form a chromogen system.

Normally the oxidase and the 4-aminoantipyrine are contained in the basic solution and phenol and a surfactant in a diluent solution.

They are remarkable improvements to the art of cholesterol analysis in not requiring freeze-drying, and enable the use of fresh enzymes. Other solutions of different composition are well known to lose activity in a week or less, even when refrigerated.

Stabilization of the enzymes useful in the determination of total cholesterol in serum may be prepared, in accordance with the invention, by dissolving the sodium salt of cholic acid in a buffer solution capable of maintaining the pH within the range of about 6 to about 8. The cholesterol esterase is added to the cholic acid dissolved in the buffer solution. The resultant mixture is thoroughly intermixed. A surfactant such as TRITON-X-100 and a polyhydroxy organic compound such as glycerol are added. A cholesterol oxidase is dissolved in a separate portion of the buffer solution and added to the mixture. If used in colormatic determination, peroxidase is also dissolved in a separate portion of the buffer solution and added to the mixture. 4-aminoantipyrine is then introduced and dissolved in the mixture. The resultant enzyme solution can then be dispensed into appropriate bottles for storage and subsequent use. Projected shelf-life of the solution in this form is from about two years to about three years.

The above enzyme solution is used in total cholesterol determinations by combining the above enzyme solution with a chromogen diluent. The diluent solution contains an appropriate color-producing agent useful in the assay of total cholesterol. A suitable color-producing chromogen diluent solution can be formulated by combining TRITON-X-100 with phenol and water. The water can be provided in a buffer solution which maintains the pH of the chromogen diluent within the same range as the above enzyme solution, such as a pH 6 to about 8. When the above enzyme solution is combined with the chromogen diluent, the resultant solution can be used directly in the assay of total cholesterol.

The combined solutions have a shelf-life of about one year under refrigerated conditions. Of course, when the total cholesterol assay is to be determined through means other than colorimetrically, the chromogen diluent solution is not necessary. In methods using oxygen consumption analysis, the above enzyme solution need only be diluted with water to have utility. In addition no peroxidase need be added.

These and many other features and attendant advantages of the invention will become apparent as the invention becomes better understood by reference to the following detailed description.

DETAILED DESCRIPTION OF THE INVENTION

The method and stabilized solutions described herein can be used in the clinical diagnostic field for the determination of total cholesterol in serum. The following chemical reaction sequence illustrates the methodology of total cholesterol determination using the stabilized solutions herein:

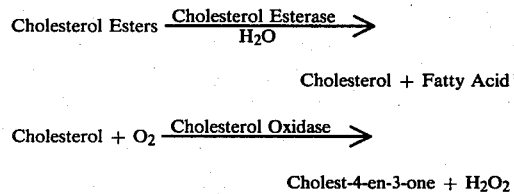

In the cholesterol assay method illustrated by the above reaction sequence, cholesterol ester bonds are split by the cholesterol esterase to form free cholesterol and the appropriate fatty acid. The cholesterol then reacts with oxygen in the presence of cholesterol oxidase to form the ketone cholest-4-en-3-one and hydrogen peroxide. It is the reaction sequence (II) above that has been developed for quantitative measurements for determining the amount of cholesterol present in a serum sample. Generally, the quantitative determination of cholesterol can be made by measuring the production of hydrogen peroxide or the consumption of oxygen.

When the production of hydrogen peroxide is used, generally a color-producing agent is used which reacts with the hydrogen peroxide to produce a chromogen providing color which is measurable quantitatively by spectrophotometric analysis. A particularly preferred method of measuring the production of hydrogen peroxide using the stabilized enzyme solutions herein is by using 4-aminoantipyrine and phenol which combines with hydrogen peroxide in the presence of a peroxidase to form a chromogen by the following reaction sequence:

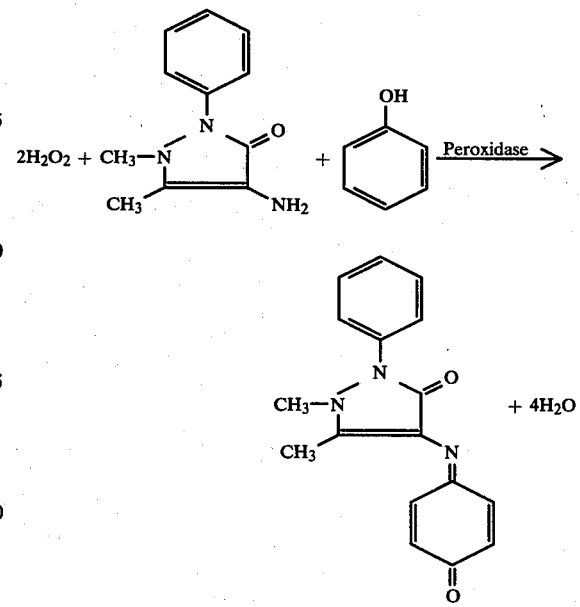

The chromogen produced has a maximum absorption at 500 nm. The intensity of light absorption at this wavelength can provide for the quantitative amount of hydrogen peroxide which, in turn, can be correlated through stoichiometric calculation to the amount of cholesterol initially present.

When cholesterol analysis is made by measuring the consumption of oxygen, the rate of oxygen consumption can be measured by an instrument which relates the amount of oxygen consumed to the total cholesterol concentration. The rate of oxygen consumption may be measured colorimetrically, however, it can also be measured using an oxygen electrode. An instrument for measuring the consumption of oxygen utilizing an oxygen electrode is available commercially from Beckman Instruments, Inc., a Cholesterol Analyzer 2. The oxygen electrode responds to oxygen concentration in the sample/reagent solution into which it is immersed. The oxygen electrode is a polargraphic electrode in that it measures a current limited by the diffusion of oxygen through a membrane to the cathode. A stable, fixed thickness of an electrolyte gel is maintained between the membrane and cathode. The amount of oxygen which diffuses through the membrane is proportional to the oxygen concentration in the solution. Associated electronic circuitry differentiates the electrode output signal providing a signal which is proportional to the rate of oxygen consumption and, thereby, to the cholesterol concentration. The oxygen consumption rate analysis is advantageous in that an instrument is commercially available which can determine and provide a direct readout of cholesterol concentration. This method also eliminates the need for a chromogen producing reaction and avoids potential interference with chromogen systems that can arise because of the presence of other colored substances within a serum sample or due to the presence of reducing substances reacting with hydrogen peroxide.

The stabilized enzyme solutions herein have applicability in both the chromogen (spectrophotometric) and oxygen consumption methods of total cholesterol determination. When the stabilized solutions herein are to be used in a spectrophotometric analysis, the enzyme solutions can be prepared as two separate reagents or as a concentrate. In the two-reagent system the first reagent, the enzyme concentrate, comprises the enzymes: cholesterol esterase; cholesterol oxidase and peroxidase in a stabilized solution in combination with providing one of the compounds, which upon coupling, forms the color producing chromogen. The second reagent, the chromogen, is also the diluent for the first reagent and comprises the second compound which, upon coupling with the first in the presence of hydrogen peroxide and peroxidase, provide the color yielding chromogen. The two separate reagents are combined to determine cholesterol concentration in serum. The two reagents have a stability, when uncombined, of about six months to one year at room temperature and two to three years under refrigeration (~4° C.) for the first reagent (concentrate) and a substantially longer lifetime for the essentially non-degradable second reagent (chromogen). When combined, the resulting mixture has a stability generally greater than state-of-the-art solutions of about 6 to about 12 months under refrigeration, about two to three months at room temperature, about one week at about 37° C. and up to about 24 hours at about 41° C. When the cholesterol assay is to be determined by oxygen consumption only one enzyme solution is needed as the determination is not predicated on the formation of color. In the oxygen consumption method of assay, the enzyme solution comprises a solution similar to the first reagent (concentrate) described with regard to the spectrophotometric assay method. That is, the enzyme solution comprises the enzymes: a cholesterol esterase and cholesterol oxidase in a stable solution. Such a stabilized solution can be diluted with water prior to use, or supplied in a final diluted form and used directly.

It has been found that the enzyme solutions herein have and retain sufficient activity to provide good precision and assay of cholesterol when formulated by the method described hereinafter.

For ease of description of the stabilized solutions, the solutions will be described herein with regard to the method in which they are to be utilized.

The buffer solutions used in formulating the reagents herein comprise a buffer solution which is capable of maintaining the pH of the reagent within a range from about 4 to about 9. A preferred buffer is prepared by dissolving potassium dihydrogen phosphate in water and adding sodium hydroxide to provide the desired pH within the above range. A particularly preferred pH for such a formulated buffer solution is a pH of about 6.60. The buffer is selected which provides the proper pH ranges and which does not materially interfere with the enzyme activity or the reactions occurring within the cholesterol assay determination. The above-described potassium dihydrogen phosphate buffer solution is particularly preferred because it provides a pH within the desired range and does not otherwise interfere with any of the enzyme reactions occurring in the cholesterol determination.

In the spectrophotometric analysis of a sample serum, the reagent containing the enzymes is prepared by dissolving the cholesterol esterase in the buffer solution having a pH within the range of about 4 to about 9. The sodium salt of cholic acid is added to assist in dissolving the cholesterol esterase in the buffer solution, and to assist in breaking up the lipoproteins in the sample which contains esters of cholesterol. Any metal salt such as an alkali metal salt of cholic acid can be used, however, the sodium salt is preferred because it is readily available commercially and the presence of the sodium ion in the solution does not deleteriously affect the solution nor the cholesterol assay. The sodium salt of cholic acid (sodium cholate) is added to the mixture of cholesterol esterase and buffer solution to provide activation of the cholesterol esterase and other enzymes to be added, to assist in the stabilization of the resulting enzyme solution, and to break up lipoproteins present in serum samples, during assay. Sodium cholate is available commercially and the commercially available sodium cholate is acceptable for use in the solutions described herein. However, the commercial preparations of sodium cholate contain some impurities which can tend to deactivate the enzymes and which can also tend to decrease the absorbance of the chromogen formed. For this reason, it is desirable to use a small amount of sodium cholate when formulating the enzyme solution. For example, sodium cholate is used in an amount up to about 15 g per liter (2.25 g/150 ml) volume of enzyme solution. It is preferred to use about 5 g per liter (0.750 g/150 ml of final enzyme solution. Such an amount of sodium cholate does not inhibit the enzyme activity to any substantial degree.

The cholesterol esterase can be any cholesterol esterase but it is preferred that the cholesterol esterase be produced from a microbial source. Such microbial produced cholesterol esterase is preferred because it has better stability and activity in the assay media than a cholesterol esterase produced from an animal source. In addition, the cholesterol esterase from a microbial source is preferred because cholesterol esterase from animal sources is generally contaminated with proteases which can react with cholesterol oxidase used in the cholesterol determination method thereby destroying the cholesterol oxidase and making it unavailable for reacting with cholesterol to produce the cholestenone. A preferred cholesterol esterase is a cholesterol esterase produced from pseudomonas fluorescens. The preferred cholesterol esterase is obtained from pseudomonas fluorescens ATCC 21156 commercially available from Kyowa Hakko Kogyo Company, Ltd.

The cholesterol esterase can be used in any amount to provide the desired activity in the enzyme solution. The activity of the cholesterol esterase desired is that amount which will provide an activity in the final enzyme solution which is sufficient to complete the deesterification of cholesterol esters in a time of about ten minutes at a temperature of about 37° C. Such an amount of cholesterol esterase can be about 150 IU for 150 ml of enzyme concentrate solution or about 1000 IU per liter of the diluted solutions used in the spectrophotometric assay. Cholesterol esterases can also be obtained from microorganisms other than pseudomonas fluorescens, for example, cholesterol esterases can be obtained from microorganisms, as described in U.S. Pat. No. 3,925,164 of Beaucamp, et al., which is incorporated herein by this reference.

Following the mixing of cholesterol esterase, sodium cholate and buffer solution, the mixture is allowed to stand under refrigeration for about 24 hours. The mixture is thoroughly mixed to obtain a homogeneously opaque solution. To this solution is added a polyhydroxy compound, such as ethylene glycol, propylene glycol, sorbitol and glycerol. Glycerol is particularly preferred as the glycerol does not inhibit the enzyme activity nor does it deleteriously affect the cholesterol assay.

The polyhydroxy compound is used in an amount up to about one-half the volume (50% by volume) of the enzyme solution or more. The amount used should be sufficient to preserve enzyme activity and to this end as little as 7.5 percent by volume of the concentrate can be used. Less can be used. The amount of polyhydroxy compound can be greater than about 50% by volume, but the amount used should be insufficient to reduce the enzyme activity so activity of the cholesterol oxidase, cholesterol esterase and if present, oxidase, make the cholesterol assay completion time longer. Greater amounts of the polyhydroxy compound can also increase the viscosity of the enzyme solution thereby making analysis by instrumental means more difficult.

A useful range for the concentrate is from about 7.5 to an amount which will not reduce enzyme activity, i.e., up to about 75 percent volume. A preferred range is from about 7.5 to about 50 percent volume. A desired range is about 25 to about 50 percent by volume.

In addition to the polyhydroxy compound, there is added a surfactant such as TRITON-X-100. TRITON-X-100 is designated in McCutcheon's "Detergents and Emulsifiers", 1973 American Edition and the 1979 combined edition Book I, both incorporated by reference as "octylphenoxy polyethoxy ethanol" having a HLB value of 13.5. It is an alkyl aryl polyether alcohol. TRITON-X-100 is a registered trademark product of Rohm & Haas, Co. and is commercially available from Eastman Kodak Co. and J. T. Baker Chemical Co. TRITON-X-100 is also known as a polyethylene glycol, p-isooctylphenyl ether, CAS registry No. 9002-93-1. For the purposes of the stabilized solutions herein, the commercially available TRITON-X-100 is acceptable. Especially acceptable is the scintillation grade TRITON-X-100 commercially available from J. T. Baker Chemical Co. and sold under the commercial name LSC Non-Ionic Surfactant Scintrex. The TRITON-X-100 can be added in an amount which will provide up to about 0.5 percent by volume in the final enzyme solution. An amount of TRITON-X-100 greater than about 0.5 percent by volume can be used, however, as the TRITON-X-100 is a surfactant, an amount greater than 0.5 percent can create excessive foaming and thereby an amount greater than 0.5 percent is undesirable. Generally, an amount of TRITON-X-100 greater than 0.3 percent by volume does not significantly increase the activity or increase the completion rate of the cholesterol assay. The TRITON-X-100 used in an amount at least about 0.1 percent by volume does activate, i.e., increase the activity of the cholesterol esterase and it has been found that the activity of cholesterol esterase from pseudomonas fluorescens exhibits a reduced activity when amounts of TRITON-X-100 are less than 0.1 percent by volume. Although not to be held to the theory herein, Applicant theorizes that amounts of TRITON-X-100 greater than 0.1 percent by volume breaks up the lipid characterization of the crude cholesterol esterase thereupon activating the cholesterol esterase.

Following the addition of the polyhydroxy compound and TRITON-X-100, a cholesterol oxidase is added to the solution. The cholesterol oxidase is first dissolved in the buffer solution and the dissolved cholesterol oxidase is then added to the enzyme solution. The cholesterol oxidase is preferably produced from microorganism sources. Cholesterol oxidases from non-microbial sources, such as animal sources, exhibit a much reduced activity in the assay media described herein for cholesterol. The microorganisms from which an acceptable cholesterol oxidase can be produced are pseudomonas sp, nocardia erythropolis and brevibacterius stero licum. Cholesterol oxidases from these microorganisms are commercially available and for the purposes of the solutions herein the commercially available cholesterol oxidases are acceptable. Although acceptable enzymes are obtained from the above microorganisms, the activity of the cholesterol oxidase in the enzyme solution depends upon the source of the cholesterol oxidase and the pH of the assay media. For the enzyme solution herein, the preferred cholesterol oxidase source is nocardia erythropolis. Such a cholesterol oxidase is commercially available from Whatman Chemical Co. The cholesterol oxidase from nocardia erythropolis is preferred as it exhibits a maximum activity at a pH of about 5 to about 9 and preferably between a pH range from about 6 to about 8. The cholesterol oxidase from nocardia erythropolis is especially stable and retains its activity in the enzyme solution herein. The cholesterol oxidase from pseudomonas sp has its maximum activity at a pH of about 5. The cholesterol oxidase produced by brevibacterium stero licum has its maximum activity at a pH of about 6. As with the cholesterol esterase, the cholesterol oxidase can be used in any amount. However, it is preferable to use the minimum amount of cholesterol oxidase for economic reasons. Larger amounts of cholesterol oxidase increase the rate of reaction and, therefore, decrease the time required to perform a total cholesterol assay. Because of the stabilizing effect of the solution herein, it has been found that the cholesterol oxidase can be present in an amount of about 300 to about 1000 IU/L of the enzyme concentrate and preferably 500 to about 750 IU/L. This amount of cholesterol oxidase is sufficient to provide a time of about ten minutes for a cholesterol assay at a temperature of about 37° C.

The peroxidase is also dissolved in a portion of the buffer solution and added to the buffered enzyme solution. A suitable peroxidase can be isolated from horseradish. Such peroxidase from horseradish is commercially available and the commercially available peroxidase is acceptable for the solutions herein. Such a peroxidase from horseradish source is available from Beckman Instruments, Inc. The peroxidase can be used in an amount such that the chromogen formation is instantaneous as the enzyme is relatively inexpensive. It is preferred to have a sufficient amount of peroxidase such that the hydrogen peroxide formed is reacted and consumed by the peroxidase substantially instantaneously and thereupon avoid any side reactions of the hydrogen peroxide. In this manner the overall schematic of the reaction is efficiently quantitative for the cholesterol determination. Generally, an amount of peroxidase of about 22.5 to about 45 KU per 150 ml of enzyme solution equal to 150 KU to 300 KU per liter of solution is sufficient to provide the instantaneous reaction with hydrogen peroxide.

To the formulated enzyme solution containing cholesterol esterase, cholesterol oxidase and peroxidase is added a compound capable of coupling through the reaction of the peroxidase and hydrogen peroxide with another compound to produce a chromogen. Only one of the compounds capable of coupling is added to the enzyme solution. The preferred compound to be added to the enzyme solution is 4-aminoantipyrine. 4-aminoantipyrine is capable of coupling with phenol in the presence of hydrogen peroxide and a peroxidase to produce a quinoneimine dye. The amount of 4-aminoantipyrine is from about 22.5 to about 67.5 mg per 150 ml total enzyme solution (150 to 450 mg/l of solution). It was found that 4-aminoantipyrine tends to inhibit the overall enzyme reaction during the cholesterol assay, as well as tending to have a destabilizing effect on the color of the chromogen produced. That is, when a greater amount of 4-aminoantipyrine is used, the more the color of the chromogen will fade and absorbance will increase at the peak absorbance of the quinoneimine dye which is at 500 nm. If less 4-aminoantipyrine is used, there is exhibited a less adverse effect on the final color, however, reducing 4-aminoantipyrine below the preferred range tends to reduce the useful dynamic range of the procedure because an insufficient amount of 4-aminoantipyrine is present to react stoichiometrically with the hydrogen peroxide produced.

The resultant-enzyme-containing solution can be used in the spectrophotometric assay of total cholesterol in a serum sample. This solution is referred to as the enzyme concentrate solution as it contains the enzymes which bring about the reaction sequence leading to the determination of cholesterol. This solution has been found to be stable with the enzymes contained therein retaining about 90 percent of their activity for about two years under refrigerated temperatures (about 4° C.) and for about four months at about room temperature.

When the enzyme concentrate solution is to be used in the spectrophotometric assay of total cholesterol, it needs to be combined with a second reagent which contains the other compound capable of coupling with the 4-aminoantipyrine and hydrogen peroxide to form a quantitatively measurable color. Such a second reagent is formed by dissolving phenol and TRITON-X-100 in water. The phenol reacts in accordance with the above-reaction sequence with the 4-aminoantipyrine and hydrogen peroxide to produce the quinoneimine dye. The amount of phenol in the second reagent is sufficient to provide for the instantaneous reaction of the hydrogen peroxide formed. However, too great a phenol concentration is undesirable as phenol tends to denature proteins in aqueous medium. Additionally, high concentrations of phenol can affect the stability of the combined reagents (enzyme concentrate and second reagent) as the phenol can react in side reactions which can produce colors even though no cholesterol is present. That is, the combined enzyme concentrate solution and second reagent can have a color due to side reactions initiated by the phenol. Preferably, the phenol concentration is from about 0.75 to about 2.25 g for 1.5 liters of the second reagent formed. Such a concentration of phenol has been found to be efficacious in the instantaneous reaction of the hydrogen peroxide formed during the cholesterol assay without substantially interfering with the colorimetric assay method or without deleteriously denaturing proteins present in the serum being treated or otherwise affecting the stabilized cholesterol assay solutions.

The water used in the solutions described herein is preferably deionized or distilled water or both. Using such deionized and/or distilled water is preferred to avoid contaminating the solution with impurities which can be present in tap water. Although tap water used by the author also yielded accurate results.

In the total cholesterol assay determination using colorimetric and spectrophotometric analysis, the enzyme concentrate solution is combined with the second reagent (chromogen producing reagent) prior to conducting the assay on a serum sample. The two solutions are combined and thoroughly intermixed prior to the assay determination. The combined mixture also exhibits a stability greater than the state-of-the-art cholesterol assay solutions. The combined mixture herein exhibits a stability of about 6 to about 12 months under refrigeration temperatures (2° to 8° C.) about two to three months at room temperature, about one week at 37° C., and about 24 hours at 41° C. The combined mixture has an initial absorbance generally less than about 0.200 and is a clear slightly reddish solution containing no solids. The pH of the combined solutions remains within the pH range of about 4 to about 9 and preferably about $6.6 \pm 0.2$.

In the total cholesterol assay of a serum sample, the enzyme concentrate solution is combined with the second reagent to produce a combined substrate solution. An aliquot of this combined substrate is combined with an aliquot of the serum sample. The two aliquots are thoroughly intermixed and incubated at about 37° C. for a time sufficient to allow reaction in the production of the quinoneimine dye. Generally, this time is preferably about 5 to 15 minutes. The time for the reaction is, as discussed above, dependent upon the media pH, the concentration of enzymes, cholate, TRITON-X-100, 4-aminoantipyrine and phenol. Alternatively, rather than combining the enzyme concentrate and second reagent to form a combined substrate solution, aliquots from each of the enzyme concentrate solution, second reagent, and serum sample can be combined and thoroughly intermixed and allowed to incubate for the necesssary time period at about 37° C. Following the incubation period there is produced a color characteristic of the quinoneimine dye. The color produced is stable for about one-half hour to one hour.

Spectrophotometric analysis is conducted using techniques of spectrophotometric analysis known to those skilled in the art. As is apparent to those skilled in the art, a blank is formed comprising the combined substrate solution. Using the blank solution, the spectrophotometer is adjusted to the combined substrate are then placed in the spectrophotometer and the absorbance for each sample is measured. The absorbance for each sample can be correlated to obtain the concentration of cholesterol therein. As stated above, the color produced in the assay media is stable for about one-half hour to one hour at room temperature which allows for ease of analysis.

The spectrophotometric analysis is calibrated by measuring absorbance of solutions of known cholesterol levels. Calibration is perfected by mixing the combined substrate with samples of known cholesterol levels and measuring the absorbance for these samples. A calibrated curve is then plotted of concentration versus absorbance. The serum sample to be analyzed can then be analyzed and its absorbance fitted to the calibrated curve to determine the total cholesterol concentration within the serum sample.

In addition to utilizing two solutions for the spectrophotometric assay of total cholesterol in serum, there can be produced one reagent containing the necessary components in a concentrate or in a final diluted form. When one solution is to be utilized, it should be kept in a container or storage area away from light to prevent increased blank absorbance. It has been found herein that such a one reagent comprising an enzyme concentrate can be formed which has a stability greater than such solutions known in the present state-of-the-art. The enzyme concentrate solution of long stability need be only diluted with water prior to use or may be supplied in the final diluted form with stability of up to one year in the spectrophotometric analysis of cholesterol in serum samples.

When a single reagent is to be employed, it can be formulated by dissolving a salt of cholic acid, such as sodium cholate in a suitable buffer solution having a pH of about 4 to about 9. A suitable buffer solution is a potassium dihydrogen phosphate and sodium hydroxide buffer solution providing a pH of about 6.60. Also dissolved in the buffer solution is the cholesterol esterase. Any suitable cholesterol esterase can be utilized, however, it is preferred to use a cholesterol esterase from a microbial source and, more preferably, from pseudomonas fluorescens, as descibed above with regard to the two-reagent system of total cholesterol assay. The components are thoroughly intermixed and allowed to stand under refrigeration for about 24 hours to insure thorough mixing.

To the solution is added a polyhydroxy compound, such as glycerol, ethylene glycol and propylene glycol in an amount up to about one-half the volume, preferably 7.5 percent by volume up to about 50 percent by volume of the final concentrate solution to be formed. A preferred polyhydroxy compound is glycerol.

A cholesterol oxidase is dissolved in a sufficient amount of the buffer solution and introduced into the mixture. The cholesterol oxidase can be any suitable cholesterol oxidase but is preferably a microbial produced cholesterol oxidase. Cholesterol oxidase produced from animal sources does not exhibit the stability of cholesterol oxidase from microbial sources. The preferred microbial sources for cholesterol oxidase are nocardia erythropolis, pseudomonas sp and brevibacterius stero licum. The amount of cholesterol oxidase added depends upon the selection of the cholesterol oxidase and the source from which it is derived. The cholesterol oxidase from nocardia erythropolis is preferred because it retains its maximum activity at a pH range from about 5 to about 9 and even retains better activity at a pH range from about 6 to about 8. The amount of cholesterol oxidase utilized is selected based upon economic considerations as the greater amount of cholesterol oxidase utilized decreases the reaction time for the total assay of cholesterol. Preferably, an amount of cholesterol oxidase, as well as cholesterol esterase, is selected which will provide a complete reaction in about two to ten minutes at about 37° C.

A peroxidase is also dissolved in a sufficient amount of the buffer solution and introduced into the enzyme concentrate solution. The peroxidase can be any suitable peroxidase and is preferably a preoxidase from horseradish source. The amount of peroxidase utilized is an amount sufficient to provide an instantaneous reaction with the hydrogen peroxide produced during the reaction sequence. By providing an instantaneous reaction with the hydrogen peroxide produced, there is avoided any side reactions of the hydrogen peroxide which could affect the specificity of the analysis.

During the addition of the polyhydroxy compound, there is also added a surfactant, e.g., TRITON-X-100 is preferred and preferably present in an amount up to about 2.5 percent by volume of the concentrate in an amount between about 0.1 to about 0.5 percent by weight. Such an amount of the TRITON-X-100 provides sufficient stability of the enzymes in the solution without providing undesirable surfactant characteristics to the resultant solution.

Following the addition of the cholesterol oxidase and peroxidase, there is added to the enzyme concentrate solution 4-aminoantipyrine. The 4-aminoantipyrine is one of the chromogen producing compounds which reacts with the hydrogen peroxide formed and phenol in the presence of the peroxidase to produce the chromogen or color-producing compound (quinoneimine dye). The amount of 4-aminoantipyrine is sufficient to react stoichiometrically with the hydrogen peroxide produced. Preferably, a stoichiometric excess of such 4-aminoantipyrine is used. The upper limit of the amount of 4-aminoantipyrine is dependent on the destabilizing effect of the 4-aminoantipyrine on the color produced, i.e., the 4-aminoantipyrine at relatively higher concentrations than the stoichiometric concentrations tend to make the color produced fade at the peak absorbance of about 500 nm for the chromogen produced.

After the addition of the 4-aminoantipyrine, phenol is added to the enzyme concentrate solution as the second compound which reacts with the 4-aminoantipyrine and hydrogen peroxide to form the chromogen. The phenol is added in an amount sufficient to react with the hydrogen peroxide formed and the 4-aminoantipyrine.

The resultant enzyme concentrate solution is diluted with water prior to use in a total cholesterol assay. The concentrate solution is stable for about six months at room temperature when kept from light. The concentrate prior to use can be diluted with distilled water generally in a ratio of about one part concentrate to about four parts water. The resulting solution is stable about 6 to 12 months at 4° C. and two to three months at room temperature.

In the oxygen-consumption method of total cholesterol assay, only one enzyme reagent is needed which is an enzyme concentrate or final diluted enzyme reagent may also be used with one year stability at 4° C. As oxygen consumption is measured to determine the quantitative amount of total cholesterol present in the serum sample, there is no need for a chromogen agent in the solution, nor is there a need for two separate solutions. The stabilized solution herein for use in the oxygen consumption analysis of total cholesterol is prepared by dissolving the sodium salt of cholic acid, such as sodium cholate, in a buffer solution having a pH range of about 4 to about 9. The buffer solution can be the buffer solution described above with regard to the total cholesterol assay using spectrophotometric analysis. After dissolving the sodium cholate in the buffer solution, cholesterol esterase is added and dissolved. The resulting mixture is allowed to stand under refrigeration conditions (2° to 8° C.) for about 24 hours to insure dissolving the components. The mixture is thoroughly intermixed to provide a homogeneously opaque solution.

The cholesterol esterase used can be any cholesterol esterase, but is preferably a cholesterol esterase from a microorganism as cholesterol esterases from animal sources do not have the stability of cholesterol esterases from microorganisms. As discussed above with regard to the cholesterol esterase used in the spectrophotometric analysis of total cholesterol, it is preferred that the cholesterol esterase be produced from the microorganism pseudomonas fluoroescens, ATCC 21156, commercially available from Kyowa Hakko Kogyo Company. Ltd.

To the cholesterol esterase buffer solution is added a polyhydroxy compound and TRITON-X-100. The polyhydroxy compound can be a polyhydroxy alcohol, such as glycerol, ethylene glycol and propylene glycol. It is preferred to use glycerol as the polyhydroxy compound. The glycerol is added in an amount that will provide about one-half the volume of the final enzyme concentrate solution. The TRITON-X-100 is added in an amount from about 0.1 to about 0.5 percent by weight of the final enzyme concentrate solution.

Following the addition of the polyhydroxy compound and surfactant, there is added to the solution a cholesterol oxidase. The cholesterol oxidase is first dissolved in a suitable amount of the buffer solution prior to introducing the cholesterol oxidase into the mixture containing the cholesterol esterase, polyhydroxy compound and surfactant. The cholesterol oxidase can be any suitable cholesterol oxidase but is preferably a cholesterol oxidase produced from a microbial source. Suitable microbial sources for the cholesterol oxidase include pseudomonas sp, nocardia erythropolis and brevibacterium stero licum. The preferred microbial source for the cholesterol oxidase is the microorganism nocardia erythropolis. The cholesterol oxidase can be present in any suitable amount but for economic reasons the amount is limited. Additionally, the amount of cholesterol oxidase used depends upon the source of the cholesterol oxidase and the pH of the resulting solution. The cholesterol oxidase produced from nocardia erythropolis is preferred because such cholesterol oxidase retains its maximum activity at a pH within the range of 5 to 9 and retains its activity preferentially within the pH range of 6 to about 8. As the amount of cholesterol oxidase is increased, the time for conducting the cholesterol assay is decreased. Preferably, it is desired to have an amount of cholesterol oxidase such that the reaction sequence leading to the consumption of oxygen is accomplished within a time limit of about 2 to 5 minutes at 37° C.

The resulting solution provides a stabilized solution which can be used in the oxygen consumption method of assay for total cholesterol in a serum sample. The enzyme concentrate solution has a stability of about two to three years under refrigerated conditions (2° to 8° C.), and a stability of about six months at room temperature. The fully diluted working solution is stable two to three months at room temperature and 6 to 12 months under refrigeration. The solution has special applicability when used in a Beckman Cholesterol Analyzer 2. The Beckman Cholesterol Analyzer 2 can conduct assay on up to about 50 samples of serum per hour. The instrument can be calibrated using standard reference serums containing known amounts of cholesterol. The volume of the serum and stabilized solution used is approximately 1 milliliter of the stabilized solution, plus approximately 5 to 10 microliters of the serum sample.

The sample introduced into the instrument is generally about five microliters in volume.

The invention is further illustrated by, but not limited to, the following examples.

EXAMPLE I

STABILIZED SOLUTIONS FOR TWO-REAGENT ASSAY OF TOTAL CHOLESTEROL BY SPECTROPHOTOMETRIC ANALYSIS

The first reagent and stabilized solution was prepared by forming a buffer solution of sodium hydroxide and potassium dihydrogen phosphate. The buffer solution was prepared by dissolving 136 g of potassium dihydrogen phosphate in 980 ml of distilled water. To the resultant solution was added 33 g of sodium hydroxide which was thoroughly intermixed and dissolved in the solution. The resulting buffer solution had a pH of about 6.60.

To 73 ml of the buffer solution was added 0.75 g of sodium cholate. Added to the buffer solution was 150 international units (IU) of cholesterol esterase from pseudomonas fluorescens (ATCC 21156), commercially available from Kyowa Hakko Kogyo Company, Ltd. The cholesterol esterase was thoroughly intermixed with the buffer solution and sodium cholate, and the resultant mixture was allowed to stand under refrigerator conditions (2° to 8° C.) for about 24 hours. The resultant mixture was a homogeneously opaque solution.

To the mixture was added 75 ml of glycerol and 2.25 ml of TRITON-X-100 (scintillation grade) from J. T. Baker Chemical Co. The glycerol and TRITON-X-100 were added simultaneously with stirring to insure thorough intermixing with the buffered cholesterol esterase mixture.

Cholesterol oxidase, commercially available from Whatman Chemical Co. and produced from the microorganism nocardia erythropolis, was dissolved in 1 ml of the buffer solution. An amount of cholesterol oxidase sufficient to provided 75 IU of activity was dissolved in the buffer solution. The resultant solution of cholesterol oxidase was introduced into the cholesterol esterase buffered solution.

Peroxidase from horseradish source in an amount sufficient to provide 22.5 KU was dissolved in 1 ml of the buffer solution. The resultant solution was also introduced into the buffered cholesterol esterase mixture.

To the buffered enzyme-containing solution was then added 45 mg of 4-aminoantipyrine. The solution was then thoroughly intermixed to dissolve the 4-aminoantipyrine. The resulting solution comprised about 150 ml total volume. The enzyme concentrate reagent had the following concentration as formulated in liter quantities:

Sodium cholate: 10 mM/l±2%
4-aminoantipyrine: 1.5 mM/l±2%
Peroxidase: 150,000 IU/l±5%
Cholesterol oxidase: 500 IU/l±5%
Cholesterol esterase: 1,000 IU/l±5%
TRITON-X-100: 1.5%±2% by volume
Glycerol: ~50% by volume
Buffered solution (pH=6.6): ~50% by volume The second reagent was formulated by dissolving 1.5 g of phenol in 1.5 liters of distilled water. To the phenol water solution was added 1.5 ml of TRITON-X-100 (scintillation grade). The resultant solution was about 1.5 liters in volume and had the following concentration as formulated:
TRITON-X-100: 0.1%±2% by volume
Phenol: 10 mM/l±2%

Prior to conducting an assay of cholesterol in a serum sample, the two reagents were combined in the following amounts. To each 0.20 ml of the enzyme concentrate reagent was added 0.80 ml of the second reagent. The combined reagents were then thoroughly intermixed by inverting at least 30 times. Thus, the formulated combined reagent had the following concentration as formulated:
TRITON-X-100: 0.4% by volume
Phenol: 8 mM
Sodium cholate: 2 mM
4-aminoantipyrine: 0.3 mM
Peroxidase: 30,000 IU/l
Cholesterol oxidase: 100 IU/l
Cholesterol esterase: 200 IU/l
Glycerol: 10.0% by volume The combined reagents had an appearance that was clear. The pH, at 25° C. for the combined reagent, was 6.7±0.2. The initial absorbance measured at 500 nm was ≦0.100. The combined reagents exhibited a linearity of ±5 percent up to 1000 mg/dl at 500 nm. The dynamic range of the combined reagents after two years of shelf life at 2° to 8° C. is estimated to be about 500 mg/dl based on accelerated stability studies at elevated temperatures. The recovery of the activity when compared with commercial lipid control serum PRECILIP was 95 to 105 percent of the theoretical value for the combined reagent.

The combined reagents provided a reaction time for assay of total cholesterol in a serum sample of about five to six minutes at 37° C. The assay of total cholesterol in a serum sample was conducted using 1.0 ml of the combined reagent with ten microliters of a serum sample.

The combined reagent had a stability at room temperature of about three months. The stability at 41° C. was about 24 hours, at 2° to 8° C. stability is estimated to be 6 to 12 months. The stability was measured to the time which would allow recovery of 95 to 105 percent of the cholesterol value of the lipid control serum PRECILIP. Five times the sample volume was used (i.e., 50 μl of sample per ml of reagent). The uncombined reagents, i.e., the enzyme concentrate reagent exhibited a stability when tested under accelerated conditions of 72 hours at 41° C. and 10 days at 37° C.

EXAMPLE II

STABILIZED ENZYME SOLUTION FOR THE SINGLE REAGENT SPECTROPHOTOMETRIC ASSAY OF TOTAL CHOLESTEROL

A buffer solution was prepared using potassium dihydrogen phosphate and sodium hydroxide as described in Example I. To 73 ml of the buffer solution was added 0.75 g of sodium cholate. Also, to the buffer solution was added 150 IU of cholesterol esterase from pseudomonas fluorescens (ATCC 21156). The mixture was thoroughly intermixed and allowed to stand under refrigeration (2° to 8° C.) for about 24 hours. The resulting solution was a homogeneously opaque solution.

To the opaque solution was added 75 ml of glycerol and 2.25 ml of TRITON-X-100 (scintillation grade) from J. T. Baker Chemical Co.

A cholesterol oxidase available commercially from Whatman Chemical Co. and produced from nocardia erythropolis was dissolved in 1 ml of the buffer solution and introduced into the buffered cholesterol esterase solution. The cholesterol oxidase was added in an amount of 75 IU. Additionally, a peroxidase in an amount of 22.5 KU was dissolved in 1 ml of the buffer solution and introduced into the buffered cholesterol esterase solution. The peroxidase was a commercially available peroxidase from horseradish source. The solution containing the cholesterol esterase, cholesterol oxidase and peroxidase was thoroughly intermixed.

To the resultant enzyme solution was added 45 mg of 4-aminoantipyrine while mixing this solution to dissolve the 4-aminoantipyrine.

Following the addition of the 4-aminoantipyrine, there was added 450 mg of phenol. The resultant solution was throughly intermixed to obtain a white, milky solution.

The resulting stabilized enzyme reagent had a concentration formulated as follows:
Sodium cholate: 10 mM/l±2%
4-aminoantipyrine: 1.5 mM/l±2%
Peroxidase: 150,000 IU/l±5%
Cholesterol oxidase: 500 IU/l±5%
Cholesterol esterase: 1,000 IU/l±5%
TRITON-X-100: 1.5%±2% by volume
Phenol: 30 mM/l±2%
Glycerol: ~50% by volume
Buffered Solution (6.6 pH): ~50% by volume The above concentrated enzyme reagent solution is reconstituted prior to performing an assay for total cholesterol by dissolving 0.20 ml of the reagent in 0.80 liters of distilled water and mixing well by inverting at least 30 times. The reconstituted solution had a stability at 2° to 8° C. for about 6 to 12 months. The reconstituted reagent had the following concentration as reconstituted:
TRITON-X-100: 0.3% by volume
Phenol: 6 mM
Sodium cholate: 2 mM
4-aminoantipyrine: 0.3 mM
Peroxidase: 30,000 IU/l
Cholesterol oxidase: 100 IU/l
Cholesterol esterase: 200 IU/l
Glycerol: ~10% by volume The above reconstituted reagent had an appearance that was clear and exhibited a pH at 25° C. of about 6.7±0.2. The initial absorbance of the reconstituted reagent was ≦0.100 at 500 nm. The reconstituted reagent exhibited a linearity at 500 nm of ±5 percent up to 1000 mg/dl. The dynamic range for the reconstituted reagent was estimated to be 500 mg/dl after one year storage at 2° to 8° C. The recovery of the reactivity for the reconstituted reagent when used to assay 5X the concentration of commercial lipid control serum PRECILIP was 95 to 105 percent of the theoretical value stated for the control (i.e., 50 μl control per 1 ml of reconstituted reagent with a reaction time of ten minutes at 37° C.

On an accelerated stability study, the reconstituted reagent exhibited a stability after storage for 24 hours at 37° C., recovered 95 to 105 percent of the 5X PRECILIP theoretical value. The concentrate reagent alone (undiluted) exhibited a stability of about 72 hours at 41° C. and about 10 days at about 37° C.

The reconstituted reagent provided a reaction time for the assay of total cholesterol of about five to six minutes at 37° C. The assay of total cholesterol was conducted using 1.0 ml of the reconstituted reagent with 10 microliters of the serum sample, or in the case of 5X PRECILIP 50 μl of PRECILIP was used per 1 ml of reconstituted reagent.

EXAMPLE III

The formulating procedure described in Example I was repeated in every essential detail with the exception that the concentration of the components was varied to provide a combined reagent having the following concentration as formulated:
Sodium cholate: 1.45 mM
4-aminoantipyrine: 0.63 mM
Phenol: 3.98 mM
TRITON-X-100: 0.038% by volume
Peroxidase: 10,000 IU/l
Cholesterol oxidase: 150 IU/l
Cholesterol esterase: 200 IU/l
Glycerol: ~10% by volume The combined reagent exhibited a stability of two months at 2° to 8° C.

EXAMPLE IV
STABILIZED SOLUTION FOR THE OXYGEN CONSUMPTION ASSAY OF TOTAL CHOLESTEROL

A buffer solution is prepared using potassium dihydrogen phosphate and sodium hydroxide as described in Example I. The buffer solution has a pH of about 6.60.

To 925 ml of the buffer solution is added 0.75 g of sodium cholate and 1000 IU of cholesterol esterase. The cholesterol esterase is from pseudomonas fluorescens (ATCC 21156). The resultant mixture is allowed to stand under refrigerated conditions (2° to 8° C.) for 24 hours to allow thorough mixing and solvation of the sodium cholate and cholesterol esterase. The resulting mixture is a homogeneously opaque solution having no large particles visible.

To the buffered cholesterol esterase solution is added 75 ml of glycerol and 2.25 ml of TRITON-X-100 (scintillation grade).

A cholesterol oxidase in an amount of about 1000 IU is dissolved in 1 ml of the buffer solution and the resultant solution introduced into the buffered cholesterol esterase solution. The resultant solution is thoroughly intermixed.

The resulting solution provides a stabilized enzyme solution which can be used in the oxygen consumption assay of total cholesterol in a serum sample. The solution has a concentration formulated as follows:
Sodium cholate: 10 mM/l±2%
Cholesterol oxidase: ~1000 IU/l±5%
Cholesterol esterase: ~1000 IU/l±5%
TRITON-X-100: 0.225%±0.2% by volume
Glycerol: 7.5% by volume
Buffer: 0.6–0.8 Molar The stabilized solution has a stability which, when measured by accelerated temperature study to the time that would allow retention of 95 to 105 percent of the cholesterol value of 5X PRECILIP, of about two to three years under refrigerated conditions, about three months at room temperature, 3 days at 37° C. and about 24 hours at 41° C.

The solution has utility in the oxygen consumption assay of total cholesterol in a serum sample when used in combination with a Beckman Cholesterol Analyzer 2. Approximately 1 ml of the solution is used in the instrument for determining total cholesterol. The serum sample to be tested is about 5 microliters which is introduced into the 1 ml of stabilized enzyme solution.

EXAMPLE V
STABILIZED ENZYME CONCENTRATE SOLUTION FOR THE OXYGEN CONSUMPTION ASSAY OF TOTAL CHOLESTEROL

A buffer solution is prepared using potassium dihydrogen phosphate and sodium hydroxide as described in Example I. The buffer solution has a pH of about 6.60.

To 73 ml of the buffer solution is added 0.75 g of sodium cholate and 150 IU of cholesterol esterase from pseudomonas fluorescens (ATCC 21156). The resultant mixture is allowed to stand under refrigerated conditions (2° to 8° C.) for 24 hours to allow thorough mixing and solvation of the sodium cholate and cholesterol esterase. The mixture is a homogeneously opaque solution with no large particles visible.

To the buffered cholesterol esterase solution is added 75 ml of glycerol and 2.25 ml of TRITON-X-100 (scintillation grade).

A cholesterol oxidase in an amount of about 150 IU is dissolved in 1 ml of the buffer solution and added to the buffered cholesterol esterase solution. The solutions are thoroughly mixed. The resulting solution provides a stabilized enzyme concentrate solution which, upon dilution with a buffer solution and/or water, can be used in the oxygen consumption assay of total cholesterol in a serum sample. The concentrate has a concentration after dilution as follows:
Sodium cholate: 10 mM±2%
Cholesterol oxidase: 1000 IU/l±5%
Cholesterol esterase: 1000 IU/l±5%
TRITON-X-100: 0.225%±0.2% by volume
Glycerol: ~50% by volume
Buffered Solution (6.6 pH): ~50% by volume The stabilized enzyme concentrate solution has utility when diluted with buffer and/or water in the instrumental analysis by oxygen consumption of total cholesterol in a serum sample such as when using a Beckman Cholesterol Analyzer 2. The enzyme concentrate solution is diluted in a ratio of about 1 part concentrate to about 5 to 6 parts diluent. Approximately 1 ml of the diluted solution is used in the instrument for determining total cholesterol. The diluted solution contained from about 7 to 8% by volume glycerol. About 5 microliters of the serum sample to be assayed is introduced into 1 ml of the diluted enzyme solution. The assay is then made on this sample.

As will be understood, the formulations disclosed herein and claimed may be used in the concentrate as claimed or diluted usually in the ratio of 4 to 6 parts by volume diluent such as distilled water per part by volume concentrate. The diluted solution will also enjoy protracted shelf life.

What is claimed is:

1. A stabilized aqueous enzyme solution for use in the determination of total cholesterol which comprises dissolved in an aqueous buffer solution having a pH of about 4 to 9, a surfactant present in an amount up to about 2.5 percent by volume of solution, and an effective amount of a salt of cholic acid, cholesterol oxidase, cholesterol esterase and a polyhydroxy organic compound present in concentration of from about 7.5 percent by volume of solution to an amount insufficient to materially reduce the enzyme activity of the cholesterol esterase and cholesterol oxidase.

2. A stabilized aqueous enzyme solution as claimed in claim 1 in which an effective amount of oxidase is present.

3. A stabilized aqueous enzyme solution as claimed in claim 2 in which an effective amount of 4-aminoantipyrine is present.

4. A stabilized aqueous enzyme solution as claimed in claim 2 in which an effective amount of phenol is present.

5. A solution as recited in claim 3 wherein the 4-aminoantipyrine is provided in an amount from about 150 to about 450 mg per liter of total stabilized enzyme solution.

6. A solution as recited in claim 1 wherein the salt of cholic acid is sodium cholate.

7. A solution as recited in claim 1 wherein the salt of cholic acid is added in an amount up to about 15 g per liter of the stabilized enzyme solution.

8. An aqueous stabilized enzyme solution for use in the determination of total cholesterol which comprises dissolved in an aqueous buffer solution having a pH range of about 4 to 9, a surfactant present in an amount up to about 2.5 percent by volume of solution and an effective amount of sodium cholate, the cholesterol esterase, cholesterol oxidase, peroxidase, 4-aminoantipyrine, phenol and a polyhydroxy organic compound in an amount of about 7.5 percent by volume of solution to an amount insufficient to materially reduce enzyme activity of said cholesterol esterase, cholesterol oxidase and peroxidase.

9. An aqueous stabilized enzyme solution as claimed in claim 1 or 8 in which the polyhydroxy organic compound is present in a concentration of from about 7.5 to about 50 percent by volume.

10. A solution as claimed in claim 1 or 8 wherein the cholesterol esterase is from the microorganism pseudomonas fluorescens ATCC 21156.

11. A solution as claimed in claim 1 or 8 wherein the cholesterol oxidase is recovered from a microorganism selected from the group consisting of pseudomonas sp, nocardia erythropolis, and brevibacterium stero licum.

12. A solution as claimed in claim 1 or 8 wherein the aqueous buffer solution comprises potassium dihydrogen phosphate and sodium hydroxide and has a pH of from about 6 to 8.

13. A solution as recited in claim 8 wherein the sodium cholate is added in an amount up to about 15 g per liter of the stabilized enzyme solution.

14. A solution as recited in claim 1 or 8 wherein the cholesterol esterase is provided at least in an amount sufficient to complete the deesterification of cholesterol esters within a time of about ten minutes at a temperature of about 37° C.

15. A solution as recited in claim 1 or 8 wherein the polyhydroxy compound is selected from the group consisting of glycerol, ethylene glycol, sorbitol and propylene glycol.

16. A solution as recited in claim 1 or 8 wherein the surfactant is provided in an amount from about 0.1 to about 0.5 percent by volume of the stabilized enzyme solution.

17. A solution as recited in claim 1 or 8 wherein the cholesterol oxidase is produced from nocardia erythropolis and the pH of the aqueous buffer solution is from about 6 to about 8.

18. A solution as recited in claim 1 or 8 wherein the cholesterol oxidase is produced from pseudomonas sp and the pH of the buffer solution is about 4 to 7.

19. A solution as recited in claim 1 or 8 wherein the cholesterol oxidase is produced from brevibacterium stero licum and the pH of the buffer solution is about 5 to 7.

20. A solution as recited in claim 1 or 8 wherein the cholesterol oxidase is provided in a total amount of about 500 to about 750 IU/liter.

21. A two-solution total cholesterol assay kit formed of an aqueous enzyme concentrate solution and a chromogen diluent solution, in which:
(a) said aqueous enzyme concentrate solution comprises an aqueous buffer solution having a pH range of about 4 to 9, a surfactant and an effective amount of a salt of cholic acid, cholesterol esterase, cholesterol oxidase, 4-aminoantipyrine, and a polyhydroxy organic compound present in an amount of about 7.5 percent by volume of the enzyme concentrate solution to an amount insufficient to reduce enzyme activity of said cholesterol esterase, cholesterol oxidase and peroxidase in combined aqueous enzyme concentrate solution and chromogen diluent solutions; and
(b) said chromogen diluent solution comprises dissolved in an aqueous solution having a pH of about 4 to 9, a surfactant and an effective amount of phenol, the total amount of surfactant present being up to 2.5 percent by volume of the combined aqueous enzyme concentrate solution and chromogen diluent solution.

22. A kit as claimed in claim 21 in which the cholesterol esterase is from the microorganism psudomonas fluorescens ATCC 21156.

23. A kit as claimed in claim 21 wherein the cholesterol oxidase is recovered from a microorganism selected from the group consisting of pseudomonas sp, nocardia, erythropolis, and brevibacterium stero licum.

24. A kit as claimed in claim 21 in which each aqueous buffer solution comprises potassium dihydrogen phosphate and sodium hydroxide and has a pH of from about 6 to 8.

25. A kit as recited in claim 21 wherein the salt of cholic acid is added in an amount up to about 15 g per liter of aqueous enzyme concentrate.

26. A kit as claimed in claim 21 in which the salt of cholic acid is sodium cholate.

27. A kit as claimed in claim 21 in which the cholesterol esterase is provided at least in an amount sufficient to complete the deesterification of cholesterol esters within a time of about ten minutes at a temperature of about 37° C.

28. A kit as claimed in claim 21 in which the polyhydroxy compound is selected from the group consisting of glycerol, ethylene glycol, sorbitol and propylene glycol.

29. A kit as claimed in claim 21 in which the surfactant is provided in a total concentration of an amount of from about 0.1 to about 0.5 percent by volume of the aqueous enzyme solution and chromogen diluent.

30. A kit as claimed in claim 21 wherein the cholesterol oxidase is produced from nocardia erythropolis and the pH of the aqueous buffer solution is from about 6 to about 8.

31. A kit as recited in claim 21 wherein the cholesterol oxidase is produced from pseudomonas sp and the pH of the buffer solution is about 4 to 7.

32. A kit as recited in claim 21 wherein the cholesterol oxidase is produced from brevibacterium stero licum and the pH of the buffer solution is about 5 to 7.

33. A kit as recited in claim 21 wherein the cholesterol oxidase is provided in a total amount of about 500 to about 750 IU/liter of aqueous enzyme concentrate solution.

34. A kit as claimed in claim 21 in which the 4-aminoantipyrine is provided in an amount of from about 150 to about 450 mg per liter of aqueous enzyme concentrate solution.

35. A stabilized aqueous enzyme solution for use in the determination of total cholesterol which comprises dissolved in an aqueous solution having a pH of about 4 to 9, a surfactant present in an amount up to about 2.5 percent by volume of solution, a salt of cholic acid present in an amount up to about 15 grams per liter of solution, cholesterol oxidase present in an amount of from about 300 to 1,000 IU/l of solution, cholesterol esterase present in an amount up to about 1,000 IU/liter of solution, and a polyhydroxy organic compound present in concentration of from about 7.5 to about 50 percent by volume of solution.

36. A stabilized aqueous enzyme solution as claimed in claim 35 in which per oxidase is present in an amount of from about 150 KU to 300 KU per liter of solution.

37. A stabilized aqueous enzyme solution as claimed in claim 36 in which 4-aminoantipyrine is present in an amount of from about 150 to about 450 mg per liter of solution.

38. A stabilized aqueous enzyme solution as claimed in claim 36 in which an effective amount of phenol is present.

39. A solution as claimed in claim 35 wherein the aqueous buffer solution comprises potassium dihydrogen phosphate and sodium hydroxide and has a pH of from about 6 to 8.

40. An aqueous stabilized enzyme solution for use in the determination of total cholesterol which comprises dissolved in an aqueous buffer solution having a pH range of about 4 to 9, a surfactant present in an amount up to about 2.5 percent by volume of solution, sodium cholate present in an amount up to about 15 grams per liter of solution, cholesterol esterase present in an amount up to about 1,000 IU per liter of solution, cholesterol oxidase present in an amount of from about 300 to 1,000 IU per liter of solution, peroxidase, present in an amount of from about 150 to 300 KU per liter of solution, 4-aminoantipyrine present in an amount of from about 150 to about 450 mg per liter of solution, an effective amount of phenol is present and a polyhydroxy organic compound in an amount of about 7.5 to about 50 percent by volume of solution.

41. A solution as recited in claim 35 or 40 wherein the polyhydroxy compound is selected from the group consisting of glycerol, ethylene glycol, sorbitol and propylene glycol.

42. A solution as recited in claim 35 or 40 wherein the surfactant is provided in an amount from about 0.1 to about 0.5 percent by volume of the stabilized enzyme solution.

43. A solution as recited in claim 1, 8, 35 or 40 wherein the surfactant is octylphenoxy polyethoxy ethanol having an HLB value of 13.5.

44. A cholesterol analysis solution which comprises from about 4 to about 6 volumes of water combined with each volume of the stabilized aqueous-enzyme solution as claimed in claim 1, 8, 35 or 40.

45. A two-solution total cholesterol assay kit formed of an aqueous enzyme concentrate solution and a chromogen diluent solution, in which:
(a) said aqueous enzyme concentrate solution comprises an aqueous buffer solution having a pH range of about 4 to 9, a surfactant and a salt of cholic acid present in an amount up to 15 grams per liter of enzyme concentrate solution, cholesterol esterase present in an amount up to about 1,000 IU per liter of solution, cholesterol oxidase present in an amount of from about 300 to 1,000 IU per liter of solution, 4-aminoantipyrine present in an amount of from about 150 to about 450 mg per liter of solution, peroxidase present in an amount of from about 150 to 300 IU per liter of solution, and a polyhydroxy organic compound present in an amount of about 7.5 percent to about 50 percent by volume of the enzyme concentrate solution; and
(b) said chromogen diluent solution comprises dissolved in an aqueous buffer solution and having a pH of about 4 to 9, a surfactant and an effective amount of phenol, the total amount of surfactant present being up to 2.5 percent by volume of the combined aqueous enzyme concentrate solution and chromogen diluent solution.

46. A kit as claimed in claim 45 in which each aqueous solution comprises potassium dihydrogen phosphate and sodium hydroxide and has a pH of from about 6 to 8.

47. A kit as claimed in claim 45 in which the polyhydroxy compound is selected from the group consisting of glycerol, ethylene glycol, sorbitol and propylene glycol.

48. A kit as claimed in claim 45 in which the surfactant is provided in a total concentration of an amount of from about 0.1 to about 0.5 percent by volume of the aqueous enzyme solution and chromogen diluent.

49. A kit including a stabilized enzyme concentrate solution and chromogen diluent solution for use in assaying total cholesterol in a sample comprising:
(a) a stabilized enzyme concentrate solution comprising an aqueous buffer solution providing a pH of about 4 to about 9 and containing an effective amount of each of sodium cholate, cholesterol esterase, cholesterol oxidase, peroxidase, 4-aminoantipyrine, a surfactant, and a a polyhydroxy compound selected from the group consisting of glycerol, ethylene glycol, sorbitol and propylene glycol; and
(b) a chromogen diluent solution comprising an aqueous solution containing an effective amount of phenol and a surfactant, the total of said surfactant provided being in an amount up to about 2.5 percent by volume of the total volume of the stabilized enzyme concentrate and chromogen diluent solution and said polyhydroxy organic compound being provided in an amount insufficient to materially reduce enzyme activity of said cholesterol esterase, cholesterol oxidase and peroxidase.

50. A kit as recited in claim 49 wherein the stabilized aqueous enzyme concentrate solution comprises 50 percent by volume of an aqueous buffer solution providing a pH of about 6.60, 50 percent by volume of glycerol, 10 mM/l±2 percent by volume of sodium cholate, 1,000 IU/l of cholesterol esterase, 500 IU/l±5 percent of cholesterol oxidase, 150,000 IU/l±5 percent peroxidase, 1.5 percent by volume of surfactant, and 1.5 mM/l±2 percent 4-aminoantipyrine and the chromogen diluent solution is aqueous and comprises 10 mM/l of phenol, 0.1 percent by volume of surfactant.

51. A cholesterol analysis solution which comprises from about 4 to about 6 volumes of water combined with each volume of assay solution formed by admixing the stabilized enzyme concentrate solution and chromogen diluent solution of claims 21, 45 or 49.

52. A kit for use in assaying total cholesterol in a sample comprising a stabilized aqueous enzyme concentrate solution which is diluted with water in a ratio of about one part enzyme solution to about four parts water prior to conducting an asay, the concentrate solution comprising about 50 percent by volume of an aqueous buffer solution providing a pH of about 6.60, about 50 percent by volume glycerol, 10 mM/l±2 percent of sodium cholate, 1,000 IU/l±5 percent of cholesterol esterase, about 1.5 percent by volume surfactant, 500 IU/l±5 percent cholesterol oxidase, 150,000 IU/l±5 percent peroxidase, 1.5 mM/l±20 percent of 4-aminoantipyrine and 30 mM/l±2 percent of phenol.

53. A kit for use in the oxygen consumption assay of total cholesterol in a sample comprising a stabilized aqueous enzyme solution comprising about 92.5 percent by volume of an aqueous buffer solution providing a pH of about 6.6, 10 mM/l±2 percent of sodium cholate, about 1000 IU/l±5 percent cholesterol esterase, 7.5 percent by volume glycerol, about 0.225 percent by volume surfactant, and about 1000 IU/l±5 percent cholesterol oxidase.

54. A kit for use in the oxygen consumption assay of total cholesterol in a sample comprising an aqueous stabilized enzyme concentrate solution which can be diluted with water in a ratio of one part enzyme concentrate to four parts water, the stabilized enzyme concentrate solution comprising about 50 percent by volume of an aqueous buffer solution providing a pH of about 6.6, about 50 percent by volume glycerol 10 MM/l±2 percent sodium cholate, and about 5333 IU/l±5 percent cholesterol esterase, about 1.5 percent by volume surfactant, and about 6,666 IU/l cholesterol oxidase.

55. A kit as recited in claim 52, 53, or 54 wherein the cholesterol esterase is from psueodmonas fluroescens.

56. A kit as recited in claim 52, 53, or 54 wherein the cholesterol oxidase is from nocardia erythropolis.

57. A method as recited in claim 21, 45, 49, 52, 53, or 54 wherein the surfactant is octylphenoxy polyethoxy ethanol having an HLB value of 13.5.

58. A cholesterol analysis solution formed by combining from about 4 to about 6 volumes of water with each volume of the stabilized enzyme concentrate solution as claimed in claim 52, 53 or 54.

59. A method of forming a stabilized enzyme solution effective for use in the determination of total cholesterol, the method comprising the steps of:
(a) preparing a buffer solution having a pH range of about 4 to 9;
(b) dissolving a salt of cholic acid in a first portion of the buffer solution;
(c) dissolving cholesterol esterase in the first portion of the buffer solution;
(d) adding a polyhydroxy organic compound selected from the group consisting of glycerol, ethylene glycol, sorbitol and propylene glycol to the first portion of the buffer solution;
(e) adding a surfactant to the first portion of the buffer solution;
(f) dissolving cholesterol oxidase in a second portion of the buffer solution and adding the dissolved cholesterol oxidase to the first portion of the buffer solution;
(g) dissolving peroxidase in a third portion of the buffer solution and adding the dissolved peroxidase to the first portion of the buffer solution; and
(h) dissolving 4-aminoantipyrine in the first portion of the buffer solution to form a stabilized enzyme solution for use in the determination of total cholesterol, said stabilized enzyme solution containing said polyhydroxy organic compound in an amount insufficient to reduce enzyme activity of said cholesterol esterase, cholesterol oxidase and peroxidase and said surfactant in an amount up to about 2.5 percent by volume of said stabilized enzyme solution.

60. A method as recited in claim 59, where the salt of cholic acid is sodium cholate.

61. A method as recited in claim 59, wherein the salt of cholic acid is added in an amount up to about 15 grams per liter of final volume of the stabilized enzyme solution.

62. A method of forming a stabilized enzyme solution effective for use in the determination of total cholesterol, the method comprising the steps of:
(a) preparing a buffer solution having a pH range of about 4 to 9;
(b) dissolving sodium cholate in a first portion of the buffer solution;
(c) dissolving cholesterol esterase in the first portion of the buffer solution;
(d) adding a polyhydroxy organic compound selected from the group consisting of glycerol, ethylene glycol, sorbitol and propylene glycol to the first portion of the buffer solution;
(e) adding a surfactant to the first portion of the buffer solution;
(f) dissolving cholesterol oxidase in a second portion of the buffer solution and adding the dissolved cholesterol oxidase to the first portion of the buffer solution containing cholesterol esterase;
(g) dissolving peroxidase in a third portion of the buffer solution and adding the dissolved peroxidase to the first portion of the buffer solution containing cholesterol esterase;
(h) dissolving 4-aminoantipyrine in the first portion of the buffer solution containing cholesterol esterase; and
(i) adding phenol to the first portion of the buffer solution containing cholesterol esterase to form a stabilized enzyme solution for use in the determination of total cholesterol, said stabilized enzyme solution containing said polyhydroxy organic compound in an amount insufficient to materially reduce enzyme activity of said cholesterol esterase, cholesterol oxidase and peroxidase and said surfactant in an amount up to about 2.5 percent by volume of said stabilized enzyme solution.

63. A method of preparing a two-solution, total cholesterol assay kit formed of an enzyme concentrate solution and a chromogen diluent solution, the method comprising the steps of:
(a) preparing a buffer solution having a pH range of about 4 to 9;
(b) preparing an enzyme concentrate solution for the assay kit by dissolving sodium cholate, cholesterol esterase, a polyhydroxy organic compound selected from the group consisting of glycerol, ethylene glycol, sorbitol and propylene glycol, and a surfactant in a first portion of the buffer solution, dissolving cholesterol oxidase in a second portion of the buffer solution and adding the dissolved cholesterol oxidase to the first portion of the buffer solution containing cholesterol esterase, dissolving peroxidase in a third portion of the buffer solution and adding the dissolved peroxidase to the first portion of the buffer solution containing cholesterol esterase, and dissolving 4-aminoantipyrine in the first portion of the buffer solution containing cholesterol esterase to form the enzyme concentrate solution; and (c) preparing a chromogen diluent solution for the assay kit by dissolving phenol and a surfactant in a fourth portion of the buffer solution wherein said surfactant is added in an amount up to about 2.5 percent volume of the total volume of said enzyme concentration solution and said chromogen diluent solution, and said polyhydroxy organic compound is added in an amount insufficient to materially reduce the enzyme activity of said cholesterol esterase, cholesterol oxidase and peroxidase.

64. A method as recited in claim 59, 62 or 63 wherein the peroxidase is from horseradish source.

65. A method as recited in claim 63 where the salt of cholic acid is added in an amount up to about 15 g per liter of volume of combined enzyme concentrate solution and chromogen diluent solution.

66. A method as recited in claim 63 wherein the surfactant is provided in an amount from about 0.1 to about 0.5 percent by volume of the combined volume of enzyme concentrate solution and chromogen diluent solution.

67. A method as recited in claim 59, 62 or 63 in which the surfactant is provided in an amount of from about 0.1 to about 0.5 percent by volume of solution.

68. A method as recited in claim 63 wherein the 4-aminoantipyrine is provided in an amount from about 150 to about 450 mg per liter of combined enzyme concentration solution and chromogen diluent solution.

69. A method of forming a stabilized enzyme solution effective for use in the oxygen consumption assay of total cholesterol, the method comprising the steps of:
(a) preparing a buffer solution having a pH range of about 4 to 9;
(b) dissolving a metal salt of cholic acid in a first portion of the buffer solution;
(c) dissolving cholesterol esterase in the first portion of the buffer solution;
(d) adding a polyhydroxy organic compound selected from the group consisting of glycerol, ethylene glycol, sorbitol and propylene glycol to the first portion of the buffer solution;
(e) adding a surfactant to the first portion of the buffer solution in an amount up to about 2.5 percent by volume of the stabilized enzyme solution and wherein said polyhydroxy organic compound is present in an amount insufficient to materially reduce enzyme activity of said cholesterol esterase and cholesterol oxidase.

70. A method as recited in claim 59, 62, 63 or 69 wherein the cholesterol esterase is from the microorganism pseudomonas fluorescens ATCC 21156.

71. A method as recited in claim 59, 62, 63 or 69 wherein the cholesterol oxidase is recovered from a microorganism selected from the group consisting of pseudomonas sp, nocardia erythropolis, and brevibacterium stero licum.

72. A method as recited in claim 59, 62, 63 or 69 wherein the buffer solution comprises an aqueous solution comprising potassium dihydrogen phosphate and sodium hydroxide providing a pH range of about 6 to 8.

73. A method as recited in claim 59, 62, 63 or 69 wherein the cholesterol esterase is provided at least in an amount sufficient to complete the deesterification of cholesterol esters in a time less than about ten minutes at a temperature of about 37° C.

74. A method as recited in claim 59, 62, 63 or 69 wherein the polyhydroxy compound is present in an amount up to about one-half of the volume of the enzymic solution.

75. A method as recited in claim 59, 62, 63 or 69 wherein the polyhydroxy compound is present in an amount from about 7.5 to about 50 percent by volume of the enzyme solution.

76. A method as recited in claim 59, 62, 63 or 69 wherein the surfactant is octylphenoxy polyethoxy ethanol having an HLB value of 13.5.

77. A method as recited in claim 59, 62, 63 or 69 wherein the cholesterol oxidase is produced from nocardia erythropolis and the pH of the buffer solution is from about 6 to about 8.

78. A method as recited in claim 59, 62, 63 or 69 wherein the cholesterol oxidase is produced from pseudomonas sp and the pH of the buffer solution is about 4 to 7.

79. A method as recited in claim 59, 62, 63 or 69 wherein the cholesterol oxidase is produced from brevibacterium stero licum and the pH of the buffer solution is about 5 to 7.

80. A method as recited in claim 59, 62, 63 or 69 wherein the cholesterol oxidase is provided in an amount of about 500 to 750 IU/liter.

* * * * *